United States Patent
Hogrefe et al.

(10) Patent No.: US 9,835,855 B2
(45) Date of Patent: Dec. 5, 2017

(54) HERMETIC SEAL AND A METHOD OF ASSEMBLING

(71) Applicant: Access Optics, LLC, Broken Arrow, OK (US)

(72) Inventors: Robert H. Hogrefe, Broken Arrow, OK (US); Thomas Mayer, White, GA (US)

(73) Assignee: Access Optics, LLC, Broken Arrow, OK (US)

( * ) Notice: Subject to any disclaimer, the term of this patent is extended or adjusted under 35 U.S.C. 154(b) by 211 days.

(21) Appl. No.: 14/681,650

(22) Filed: Apr. 8, 2015

(65) Prior Publication Data

US 2015/0286051 A1  Oct. 8, 2015

Related U.S. Application Data

(60) Provisional application No. 61/976,905, filed on Apr. 8, 2014.

(51) Int. Cl.
| | |
|---|---|
| *G02B 27/00* | (2006.01) |
| *B32B 37/06* | (2006.01) |
| *B32B 37/14* | (2006.01) |
| *B32B 37/10* | (2006.01) |
| *B32B 37/18* | (2006.01) |
| *B32B 37/04* | (2006.01) |
| *A61B 1/00* | (2006.01) |
| *G02B 7/02* | (2006.01) |
| *G02B 23/24* | (2006.01) |

(52) U.S. Cl.
CPC ........ *G02B 27/0006* (2013.01); *A61B 1/0011* (2013.01); *A61B 1/00096* (2013.01); *B32B 37/04* (2013.01); *B32B 37/06* (2013.01); *B32B 37/10* (2013.01); *B32B 37/142* (2013.01); *B32B 37/18* (2013.01); *G02B 7/025* (2013.01); *G02B 23/2423* (2013.01); *G02B 23/2492* (2013.01); *B32B 2307/412* (2013.01); *B32B 2535/00* (2013.01); *B32B 2551/00* (2013.01)

(58) Field of Classification Search
CPC ..... G02B 27/0006; B32B 37/18; B32B 37/04; B32B 37/142; B32B 37/10; B32B 37/06
See application file for complete search history.

(56) References Cited

U.S. PATENT DOCUMENTS

| | | |
|---|---|---|
| 3,904,278 A | 9/1975 | Hummel |
| 4,778,253 A | 10/1988 | Siga et al. |
| 2010/0200061 A1* | 8/2010 | Melchior ................ B29C 63/04 136/256 |

FOREIGN PATENT DOCUMENTS

JP   2009014929   1/2009

* cited by examiner

*Primary Examiner* — Daniel Lee
(74) *Attorney, Agent, or Firm* — Gable Gotwals

(57) ABSTRACT

A hermetic seal between an optical element and a metal mount or housing using a fluoropolymer. The fluoropolymer is dispersed along the interior edge of the metal mount. The metal mount and fluoropolymer are then heated to a temperature exceeding the melting point of the fluoropolymer. Once heated the optical element is pressed into the metal mount and allowed to cool. The metal mount, optical element and thickness of fluoropolymer are sized to provide an interference fit between the metal mount and optical element.

11 Claims, 4 Drawing Sheets

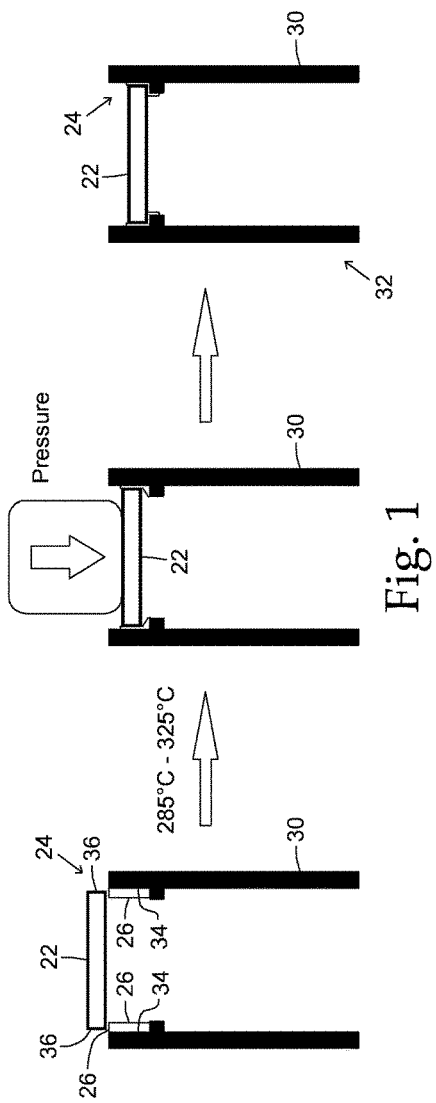
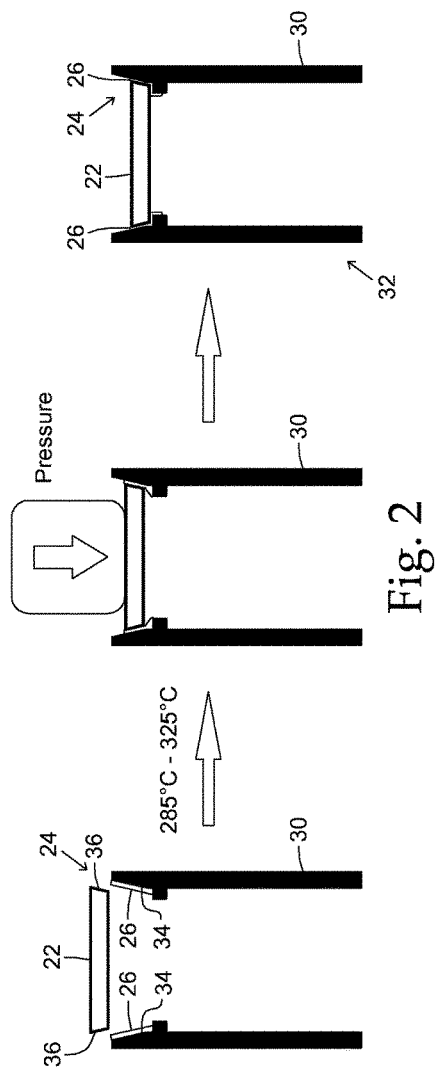

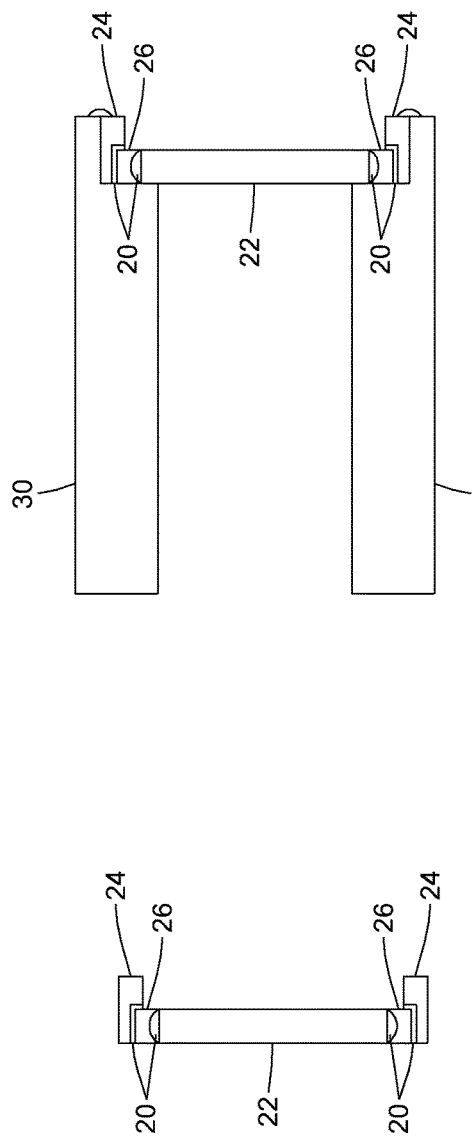
Fig. 3
Fig. 4
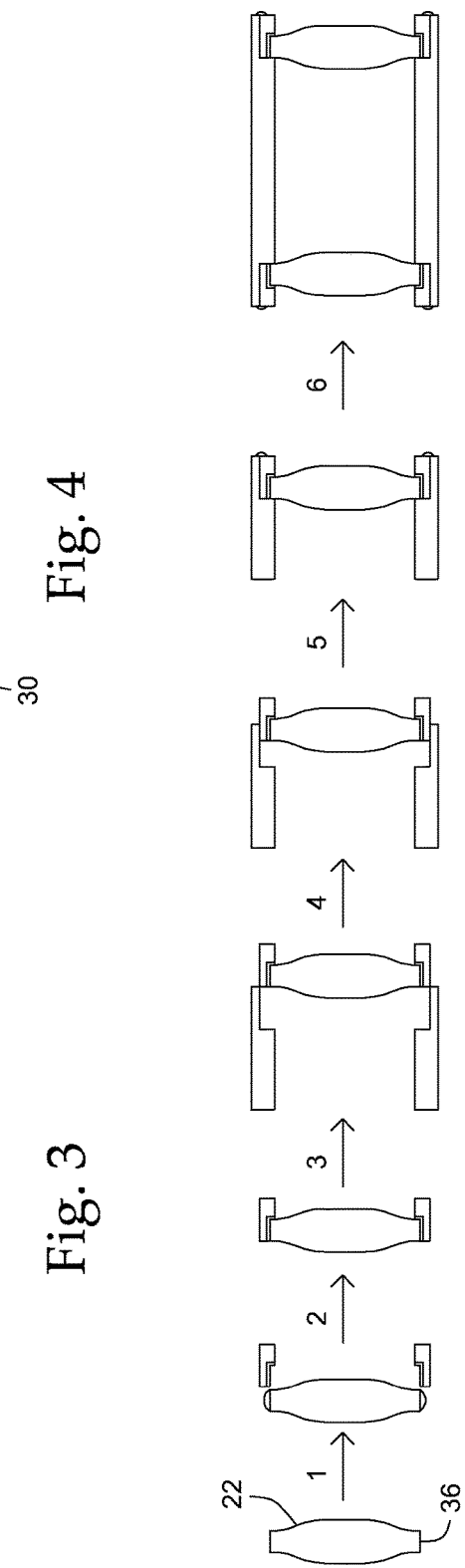
Lens - Ring Mount with Tube Weld
Fig. 5

Window – Ring Mount with Tube Weld

Window – Tube Mount

Window – Tube Mount with Crimp

Window - Ring-in-Ring Mount Double Tube Weld

Window - Tube Mount No Primer

HERMETIC SEAL AND A METHOD OF ASSEMBLING

CROSS-REFERENCE TO PENDING APPLICATIONS

This application claims the benefit of U.S. Prov. Pat. Appl. No. 61/976,905 for A Hermetic Seal And A Method For Assembling, filed Apr. 8, 2014.

FIELD OF THE INVENTION

The present invention relates generally to method for sealing an optical element to a metal housing. More particularly, the present invention relates to a method for providing a moisture tight seal between an optical element and a metal frame capable of withstanding multiple cycles of sterilization in an autoclave.

BACKGROUND OF THE INVENTION

Many medical procedures have been improved over the past decades by the use of arthroscopic devices. Treatments that once required invasive procedures and extended hospital stays are routinely done on an outpatient basis with an abbreviated recovery period. Endoscopes alone and in combination with imaging systems are used for arthroscopy as well as other diagnostic procedures. The endoscopes and optical couplers sometimes used to connect the endoscope to an imaging system must be sterilized before they can be used in an evasive procedure.

The most common, quickest, and cost effective way to sterilize a piece of equipment is to use an autoclave. This subjects the tool to a high pressure, high temperature and high moisture environment proven to effectively kill pathogens.

The surfaces of the optical elements used in these tools should have no debris or substance on them that will obscure or degrade the quality of the image they are transmitting. The optical elements are positioned within a metal tube or sheath and isolated from the environment by sealing the ends of the sheath. Typically, an optical element with metalized edges is used to seal the ends of the sheath or tube. The metalized edges of the optical element are brazed or soldered into the sheath or tube to form the hermetic seals.

As can be imagined subjecting these optical tools to the environment inside of an autoclave can be detrimental to its longevity if moisture were to breach the hermetic seals. If sufficient moisture penetrates the seals to allow condensation on the internal surfaces of the optical element it will distort the view provided by the optics. If the optical elements contained within the sheath can be chemically attacked by moisture that has condensed on their surfaces the distortion to the view will be permanent and remain if the condensation dissipates.

Various methods of securing an optical element in an autoclavable optical tool are known. These include braising, fritting, O-rings, adhesive and brazing. However, each of these methods have their disadvantages. These disadvantages range from cost and labor required to short life cycles.

What is needed is a method for mounting an optical element or window into an optical train that is quick, inexpensive, easy to assemble and provides a reasonable life cycle.

BRIEF SUMMARY OF THE INVENTION

The present invention achieves its objectives by providing a hermetic seal between an optical element and a metal mount or housing using a fluoropolymer. The fluoropolymer is dispersed along the interior edge of the metal mount or on the optical element. The metal mount and fluoropolymer are then heated to a temperature exceeding the melting point of the fluoropolymer. Once heated the optical element is pressed into the metal mount and allowed to cool. The metal mount, optical element and thickness of fluoropolymer our sized to provide an interference fit between the metal mount and optical element.

The present invention may be used in various configurations including the metal mount is part of the tubular metal housing forming the optical train or where the optical element mounted in the metal mount is further secured to a tubular metal housing by brazing or welding the metal mount to the metal housing.

The present invention provides an inexpensive, effective and rigorous way to mount optical elements for application where it will be subjected to autoclave sterilization or where containing or excluding water or moisture is desired.

BRIEF DESCRIPTION OF THE DRAWINGS

Preferred embodiments of the invention will now be described in further detail. Other features, aspects, and advantages of the present invention will become better understood with regard to the following detailed description, appended claims, and accompanying drawings (which are not to scale) where:

FIG. 1 is a progression of the drawings showing the preferred embodiment of the present invention used on an optical element;

FIG. 2 is a progression of the drawings showing another embodiment of the present invention used on an optical element FIG. 3 is a cross sectional view of one embodiment of the optical element mount of the present invention;

FIG. 4 is a cross sectional view of the optical element mount of FIG. 1 secured in a metal housing;

FIG. 5 is a progression of the drawings showing the present invention used on an optical element;

DETAILED DESCRIPTION OF THE INVENTION

Figure 6:
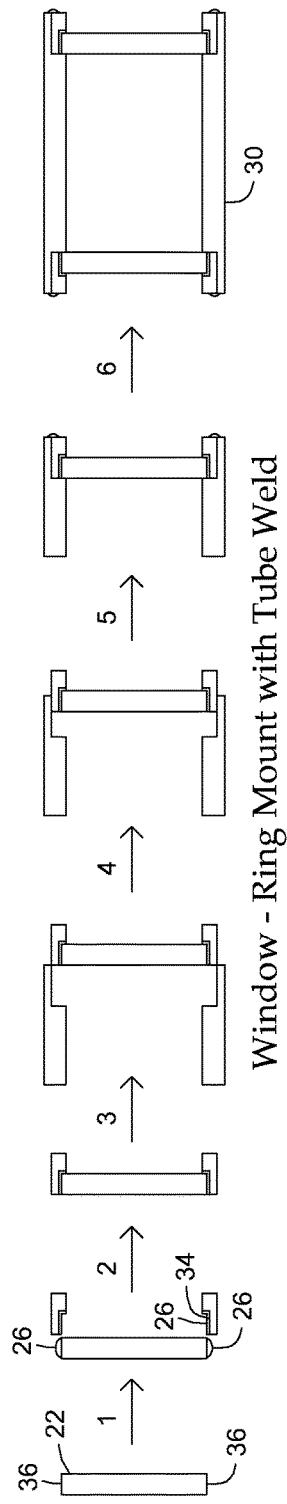
FIG. 6 is a progression of the drawings showing the present invention used on a window.

The present invention provides a cost effective and durable seal between an optical element 22 and metal mount 24 by using a crystalline or semi-crystalline fluoropolymer, chloropolymer, fluorochloropolymer, copolymers of fluoropolymer, chloropolymer, and fluorochloropolymer or Parylene N, a non-halogenated poly(para-xylene), that have high moisture barrier properties and a crystalline melting point above 145° C. In the preferred embodiment a ceramic, sapphire or glass optical element 22 is held in a metal mount 24 by a fluoropolymer 26. The optical element 22 is generally circular, but may be any regular or irregular shape. The metal mount 24 surrounds the optical element. This metal mount 24 may be the end portion of a tubular metal housing 30 that forms the optical train 32 as seen in FIGS. 1, 2, 6, 7, and 10.

In other embodiments the metal mount 24 functions as a frame which holds the optical element 22. The metal mount 24 is then secured to a tubular metal housing 30 by a weld 28 or brazed joint between the metal mount 24 and the metal housing 30. See FIGS. 3, 4, 5 and 6 In other applications the optical element 22 and metal mount 24 may be secured to the tubular metal housing 30 by crimping the end of the metal housing 30 over the edge of the metal mount 4 and/or optical element 22.

In the preferred embodiment a fluoropolymer 26 including but not limited to chlorotrifluoroethylene polymer, copolymer of tetrafluoroethylene and perfluoroalkoxyethylene, polyvinyl fluoride, Parylene C, Parylene D, and Parylene HT, ETFE (Alternate names, poly(1,1,2,2-tetrafluorobutane-1,4-diyl), poly(ethene-co-tetrafluoroethene,ethylene tetrafluoroethylene) powder such as ETFE Powder Topcoat, clear or pigmented manufactured by E.I. du Pont de Nemours & Company, Wilmington, Del.), is applied to the seal area surface 34 of a metal mount 24. The ETFE powder can be applied by any number of methods including but not limited to, spreading or suspension or paste of the ETFE power in a liquid carrier such as xylene, electrostatic deposition from a fluidized ETFE particle bed on to the heated seal area surface 34, or other know methods to deposit thermoplastic coating to metal substrates. In addition to powder form, Fluoropolymers 26 in tape or sheet form may be used for the present invention.

The ETFE can be applied to the metal mount 24, optical element 22, or both metal mount sealing area surface 34 and optical element's 22 sealing surfaces 36. The ETFE powder coated sealing surfaces 34 and/or 36 are heated in an oven to at about 285° C. for 10 to 15 minutes or a period of time sufficient to fuse the ETFE particles. After fussing the ETFE to the sealing surfaces 34 and/or 36 the optical element 22 and metal mount 24 are positioned such that they can be pressed together for form a seal when pressure is applied to either or both elements See FIG. 1.

Prior to pressing the optical element 22 into the metal mounting 24, they are heated until the fluoropolymer melts (285° C.-325° C. for ETFE resin). When the fluoropolymer 26 melts pressure is applied to the optical element 22 and/or metal mount 24 to push the optical element 22 into the metal mount 24 forcing the viscous resin to flow over and contact the optical element 22 and metal mount 24 on the seal surfaces 34 and 36. After they are sealed they are allow to cool to room temperature.

In the preferred embodiment the uncoated clearance between the optical element 22 and metal mount 24 can range between 1 micron and 100 microns with the optimum clearance between 7 microns and 25 microns. The applied thickness of ETFE should be sufficient to form a continuous layer of ETFE between the two surfaces to be sealed. The combined thickness of the fused fluoropolymer 26 on the metal mount sealing surface 34 should be between 5 microns and 500 microns thicker than the clearance between the metal mount sealing surface 34 and optical mount sealing surface 36 before the application of the resin.

One skilled in the art will recognize that the fluoropolymers 26 listed have some level of permeability and that the width and thickness of the seal area will have some impact on the level hermeticity of the seal. We have found that seals having a width less than 100 microns and an average thickness of at least 15 microns will typically have a helium leak rate between $1 \times 10^{-9}$ to $1 \times 10^{-8}$ atm.cc/sec and pass 500 autoclave cycles.

Seals made with substrates where one or both seal surfaces are at slight angle the to the to the direction of substrate insertion increase the percentage of continuous seal area. Thus in one embodiment of the invention the sealing surface 34 of the metal mount 24 is chamfered. In this embodiment the sealing surface 36 of the optical element 22 may be chamfered as well. The chamfer angle of these sealing surfaces 34 and 36 would preferably be the same. See FIG. 2.

In another embodiment of the substrates are prepared as explained above are heated above the melting point of the fluoropolymer 26 and seated together while one of the substrates was rotated between 15° and 90° perpendicular to the direction of insertion over the distance between where the resin layer of one substrate first made contact with the other substrate and where the maximum thickness of the seal is achieved. This twisting action increase the amount of and introduces a second direction of shear experienced by the molten resin, increasing the amount of intimate contact between the resin and substrates.

Other embodiments of the present invention start by applying a primer coat 20 to the interior surface of the metal mount 24 and the peripheral edge of the optical element 22. This involves applying a dispersion of a fluoropolymer 26 to the interior surface of the metal mount 24 and the peripheral edge of the optical element 22. The metal mount 24 and optical element 22 are then heated to above the melting point of the fluoropolymer to adhere the primer coat to the metal mount 24 and the optical element 22. It is heated within a range of 285° to 325° C. for a time sufficient to sinter the deposited primer particles.

The optical element 22 and metal mount 24 are allowed to cool. A film or tape of fluoropolymer material 3 is wrapped around the exterior peripheral edge of the optical element 22. The metal mount 24 is then heated rapidly to a temperature within a range of 285° to 325° C. in a non-oxidative atmosphere or vacuum. The optical element 22 is then pressed into the metal mount 24 by a mechanical means. The thickness of the fluoropolymer 26 is in excess of the amount sufficient to provide an interference fit between peripheral edge of the optical element 22 and the interior of the metal mount 24 and hold the optical element 22 in place.

Once the optical element 22 is secured in the metal mount 24, the assembly can be inserted into a metal housing 30 of an endoscope or other optical device. The assembly is secured to the tubular metal housing 30 by a weld 28 along the interface between the metal mount 24 and the metal housing 30.

The present invention can also be adapted to installing an optical element 22 directly into the tubular metal housing 30 or a tube mount. See FIG. 7. In this embodiment the primer coat 20 is applied directly to the interior of the metal mount 24 of the tubular metal housing 30 and the outer periphery of the optical element 22. These parts are then heated to a temperature above the melting point of the fluoropolymer primer. The pieces are allowed to cool. Once cooled the exterior periphery of the optical element 22 is wrapped with a film or tape of fluoropolymer 26. The optical element 22 is then pressed into an interference fit in the metal mount 24 of the tubular metal housing 30.

Figure 7:
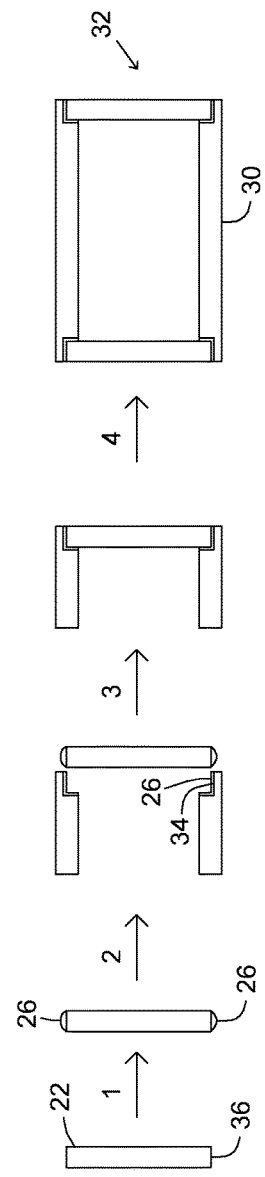
FIG. 7 is a progression of drawings showing a cross sectional view of another embodiment of the optical element mount of the present invention.
Figure 8:
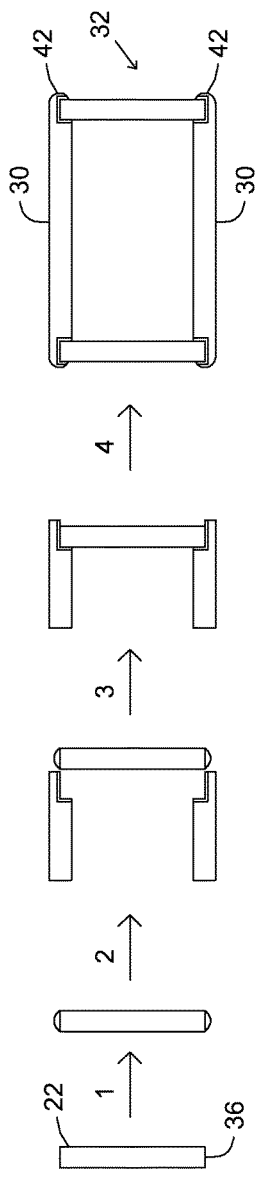
FIG. 8 is a progression of drawings showing a cross sectional view of another embodiment of the optical element mount of the present invention.

The tube mount shown in FIG. 7 can be further improved by crimping the ends of the tube mount down over the fluoropolymer 26 and the outer peripheral edge of the optical element 22. See FIG. 8. This ensures the optical element 22 is retained in the tube mount.

Figure 9:
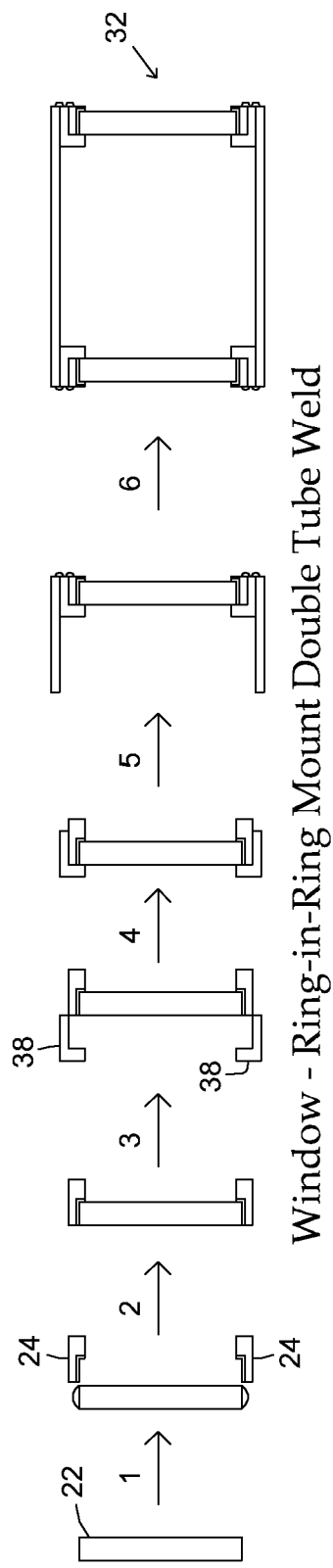
FIG. 9 is a progression of drawings showing a cross sectional view of another embodiment of the optical element mount of the present invention.

FIG. 9 shows another embodiment of the present invention. Here the optical element 22 is mounted in the metal mount 24 as first explained above. A second ring 38 is placed around the outer periphery of the metal mount 24. The metal mount 24 extends across the fluoropolymer 26 and onto the first face of the optical element 22. The second ring 38 extends across the metal mount 24, fluoropolymer 26 and on to the opposing or second face of the optical element 22. This assembly is then secured to the metal housing 30 by a first weld 28 located at the interface of the metal mount 24 and the second ring 38 and a second weld 40 located at the interface between the second ring 38 and the metal housing 30.

Figure 10:
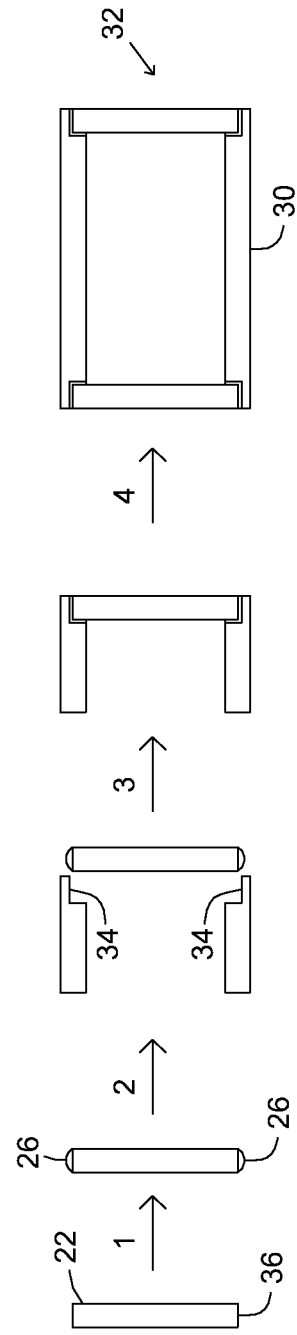
FIG. 10 is a progressive drawing showing a cross section view of another embodiment of the optical element mount of the present invention.

FIG. 10 shows another embodiment of the present invention. In this embodiment no primer coat is applied to the metal mount 24 of the tubular metal housing 30 or the outer periphery of the optical element 22. The periphery of the optical element 22 is wrapped with a fluoropolymer tape or film 26, formed by coating the edges of the optical element 22 with a solvent solution or particle dispersion of one of the herein polymer material of this invention. The metal mount 24 of the tubular metal housing 30 is heated to within a range of 285° to 325° C. in air, vacuum, or non-oxidizing atmosphere. The optical element 22 is then pressed into an interference fit in the tube mount while the tube is within a range of 285° to 325° C. As soon as the optical element 22 contacts the metal mount 24 of the tubular metal housing 30, the metal housing 30 is immediately removed from the heat source and allow to cool by convection.

The present invention has numerous benefits that are not possible with prior art methods for securing an optical element 22 into an autoclavable or hermetic device. The present invention allows for coating of the optical element 22 before it is mounted.

If the mounted optical element 22 assembly of the present invention does not pass quality control requirements or is otherwise defective, the optical element 22 may be removed from the mount 24 and reused.

Glass, quartz or sapphire optical elements may be mounted using the present invention.

The present invention does not require any machining once the optical element 22 is mounted.

Standard helium leak testing can be used to check the seal of the present invention mountings. More costly testing methods are not necessary.

The interface between the optical element 22 and the housing or mounts is cushioned by the fluoropolymer material. This protects the optical element 22 from thermal shock during sterilization and mechanical shocks arising from mishandling of the assembly.

The finished assemblies are commonly used on medical devices. Fluoropolymers 26 as well as the materials used for the optical element 22, metal mount 24 and metal housing 30 are all biocompatible. Thus related complications are avoided.

Finally the cross sectional area of the fluoropolymer 26 presented to the face of the optical element 22 and optical train 32 and subjected to moisture is much smaller than the area of a comparable O-ring seal. The present invention also has a longer avenue of penetration for moisture to travel than comparable O-ring seals. Thus it is harder for moisture to penetrate the seal of the present invention than it is to penetrate an O-ring seal. This results in reduced moisture penetration and a longer service life for the device.

Microscopic voids exist on the surfaces of both the metal mount 24 and optical element 22. The ability of the material typically used for O-rings to fill these voids is limited by the elastic properties of the O-ring. Moisture can migrate through these the voids between the interface of the O-ring and the tube and optical element.

The process of melting the fluoropolymer 26 in contact with the seal surface 34 of the metal mount 24 and the seal surface 36 of the optical element 22 surfaces, combined with the low surface tension of the melted fluoropolymer 26, results in the fluoropolymer 26 being able to effectively wet and flow into these microscopic voids present on the metal mount 24 and optical element 22 surfaces. Filling and bonding to the seal surface 34 and 36 voids by the molten fluoropolymer 26 prevents the migration of moisture through the voids between the fluoropolymer 26, metal mount 24 and optical element 22 interface.

The foregoing description details certain preferred embodiments of the present invention and describes the best mode contemplated. It will be appreciated, however, that changes may be made in the details of construction and the configuration of components without departing from the spirit and scope of the disclosure. Therefore, the description provided herein is to be considered exemplary, rather than limiting, and the true scope of the invention is that defined by the following claims and the full range of equivalency to which each element thereof is entitled.

What is claimed is:

1. A method for hermetically sealing an optical element to a metal mount of a metal housing, said method comprising:
    applying a fluoropolymer to a sealing surface of the metal mount;
    heating the fluoropolymer and the metal mount to a temperature above the fluoropolymer's melting point; and
    pressing an optical element having a sealing surface into the metal mount;
    wherein the optical element, metal housing and thickness of fluoropolymer are sized to provide an interference fit between the optical element and the metal mount.

2. The method of claim 1 wherein the fluoropolymer is selected from the group consisting of: fluorochloropolymer, Parylene N, non-halogenated poly(para-xylene), chlorotrifluoroethylene polymer, copolymer of tetrafluoroethylene perfluoroalkoxyethylene, polyvinyl fluoride, Parylene C, Parylene D, and Parylene HT.

3. The method of claim 1 further comprising rotating the optical element relative to the metal mount as the optical element is pressed into the metal mount.

4. The method of claim 3 further comprising rotating the optical element in a range of 15° to 90° relative to the metal mount while pressing the optical element into the metal mount.

5. The method of claim 1 wherein the fluoropolymer and the metal mount are heated to within a range of 285° C. to 325° C.

6. The method of claim 5 further comprising retaining the fluoropolymer and the metal mount within a range of 285° C. to 325° C. for 10 to 15 minutes.

7. The method of claim 1 further comprising cooling the optical element, metal mount and fluoropolymer to room temperature.

8. The method of claim 1 further comprising:
    chamfering the seal surface of the metal mount; and
    chamfering the seal surface of the optical element.

9. The method of claim 8, wherein the angle of chamfer of the seal surface of the metal mount is the same as the angle of chamfer of the seal surface of the optical element.

10. The method of claim 1 further comprising providing an uncoated clearance within a range of 1 micron to 100 microns between the sealing surface of the optical element and the sealing surface of the metal mount.

11. The method of claim 1 further comprising providing a thickness of the fluoropolymer on the metal mount sealing surface of between 5 microns and 500 microns thicker than a clearance between the metal mount sealing surface and the optical element sealing surface.

\* \* \* \* \*